United States Patent
Abe et al.

(10) Patent No.: US 9,966,706 B2
(45) Date of Patent: May 8, 2018

(54) CONNECTOR DEVICE (71) Applicant: OMRON CORPORATION, Kyoto-shi, Kyoto (JP)

(72) Inventors: Fumiaki Abe, Amagasaki (JP); Satoshi Takamori, Yokohama (JP)

(73) Assignee: OMRON CORPORATION, Kyoto-shi (JP)

( * ) Notice: Subject to any disclaimer, the term of this patent is extended or adjusted under 35 U.S.C. 154(b) by 0 days. days.

(21) Appl. No.: 15/327,494

(22) PCT Filed: Jul. 2, 2015

(86) PCT No.: PCT/JP2015/069123
§ 371 (c)(1),
(2) Date: Jan. 19, 2017

(87) PCT Pub. No.: WO2016/031389
PCT Pub. Date: Mar. 3, 2016

(65) Prior Publication Data
US 2017/0207584 A1    Jul. 20, 2017

(30) Foreign Application Priority Data
Aug. 29, 2014 (JP) ................. 2014-176429

(51) Int. Cl.
*H01R 13/71* (2006.01)
*A61B 8/00* (2006.01)
(Continued)

(52) U.S. Cl.
CPC .............. *H01R 13/71* (2013.01); *A61B 8/44* (2013.01); *H01R 13/2421* (2013.01); *H01R 13/629* (2013.01)

(58) Field of Classification Search
CPC ................ H01R 13/6215; H01R 11/18; H01R 13/2421; H01R 13/2428; H01R 13/639
(Continued)

(56) References Cited

U.S. PATENT DOCUMENTS 5,676,560 A    10/1997  Endo et al.
5,993,240 A *  11/1999  Schaefer ............ H01R 13/6215
                                                    439/352
(Continued)

FOREIGN PATENT DOCUMENTS

DE    102011055963 A1    6/2013
JP    S58-148888 U       10/1983
(Continued)

OTHER PUBLICATIONS

The English translation of the international preliminary report on patentability (Chapter I) of PCT/JP2015/069123 mailed by the International Bureau of WIPO dated Mar. 9, 2017.
(Continued)

*Primary Examiner* — Tulsidas C Patel
*Assistant Examiner* — Marcus Harcum
(74) *Attorney, Agent, or Firm* — Metrolexis Law Group, PLLC (57) ABSTRACT

A switching connector includes a probe-side connector including a plurality of probe pins, a housing-side connector including a plurality of electrode pads, and a motor configured to cause a contact state and a non-contact state to be switched, by causing the plurality of probe pins and/or the plurality of electrode pads to move parallel to a direction in which the probe-side connector and the housing-side connector face each other.

12 Claims, 9 Drawing Sheets

(51) Int. Cl.
*H01R 13/24* (2006.01)
*H01R 13/629* (2006.01)

(58) Field of Classification Search
USPC .................................. 439/700, 362, 364
See application file for complete search history.

(56) References Cited

U.S. PATENT DOCUMENTS

| | | | | |
|---|---|---|---|---|
| 6,257,918 B1* | 7/2001 | Yamamoto | ......... | H01R 13/6315 |
| | | | | 439/34 |
| 7,256,593 B2* | 8/2007 | Treibergs | ............ | G01R 1/0466 |
| | | | | 324/754.05 |
| 7,465,195 B1* | 12/2008 | Kerrigan | ................ | H01R 23/68 |
| | | | | 439/607.05 |
| 7,740,489 B2* | 6/2010 | Trout | ................... | H01R 12/523 |
| | | | | 439/74 |
| 8,033,872 B2* | 10/2011 | Yang | .................... | H01R 12/714 |
| | | | | 439/66 |
| 9,666,981 B1* | 5/2017 | Bell | .................... | H01R 13/6215 |
| 2002/0068476 A1* | 6/2002 | Kakinoki | ........... | H01R 13/6215 |
| | | | | 439/362 |
| 2002/0151207 A1* | 10/2002 | Bates, III | ............. | G02B 6/3878 |
| | | | | 439/364 |
| 2005/0070145 A1* | 3/2005 | Huang | ................ | H01R 13/639 |
| | | | | 439/246 |
| 2006/0279301 A1 | 12/2006 | Treibergs | | |
| 2010/0194419 A1* | 8/2010 | Chan | .................. | G01R 1/07328 |
| | | | | 324/756.05 |
| 2012/0282813 A1* | 11/2012 | Ballard | ............. | H01R 13/6215 |
| | | | | 439/638 |
| 2013/0095685 A1* | 4/2013 | Rassoolkhani | ...... | H01R 13/639 |
| | | | | 439/345 |
| 2015/0064977 A1* | 3/2015 | Higgy | .................... | H01R 9/032 |
| | | | | 439/655 |
| 2015/0349459 A1* | 12/2015 | Tsang | ..................... | H01R 13/46 |
| | | | | 439/365 |
| 2016/0104956 A1* | 4/2016 | Santos | ................ | H01R 9/0518 |
| | | | | 324/754.03 |

FOREIGN PATENT DOCUMENTS

| | | |
|---|---|---|
| JP | H03-158141 A | 7/1991 |
| JP | H06-38919 U | 5/1994 |
| JP | H08-045609 A | 2/1996 |
| JP | H08-171974 A | 7/1996 |

OTHER PUBLICATIONS

The International Search Report dated Oct. 6, 2015 for PCT/JP2015/069123.
The Korean Office Action dated Jan. 15, 2018 in a counterpart Korean patent application.
EESR dated Mar. 6, 2018 in a counterpart European Patent application.

* cited by examiner

CONNECTOR DEVICE

TECHNICAL FIELD

The present invention relates to a connector device, particularly to a connector device via which a probe and a main device of an ultrasonograph are connected to each other.

BACKGROUND ART

Ultrasonographs utilizing ultrasonic waves have been widely used in the medical field. An ultrasonograph generally includes (i) an ultrasonic probe which transmits and receives an ultrasonic wave and (ii) a main device (housing).

The ultrasonograph operates as follows. That is, (i) the ultrasonic probe transmits an ultrasonic wave, which is generated by transducers included in the ultrasonic probe, to a diagnostic target, (ii) the ultrasonic probe then receives a reflected ultrasonic wave, and (iii) the main device electrically processes a received signal, which is based on the reflected ultrasonic wave, so as to create an ultrasonic image.

Generally, such an ultrasonograph includes a plurality of ultrasonic probes, and any one of the plurality of ultrasonic probes is selected in accordance with a diagnostic target. For this reason, an ultrasonograph is generally provided with a switching section for switching between ultrasonic probes to be used. According to a current general ultrasonograph, such a switching section is realized by relay circuits mounted on a substrate.

Such relay circuits, however, cause the following problem. Specifically, since it is necessary to provide relay circuits depending on the number of transducers included in each of ultrasonic probes, a size of a substrate may become large. This can make it difficult to downsize an entire ultrasonograph. Furthermore, there is a problem that multi-layering of substrates, on each of which a relay circuit(s) is/are provided, causes the substrates to be expensive.

To address the above problem, Patent Literature 1 discloses providing a probe connector, via which an ultrasonic probe and a main device of an ultrasonograph are connected to each other, with a switching section that switches between (i) a connected state where the ultrasonic probe and the main device are connected to each other and (ii) a non-connected state where the ultrasonic probe and the main device are not connected to each other. According to the probe connector disclosed in Patent Literature 1, the connected state and the non-connected state are switched by, with use of a drive motor, causing probe-side electrodes to move so that the probe-side electrodes are connected to or separated from respective housing-side electrodes. This eliminates the need for providing the ultrasonograph with a relay circuit, and thereby allows a reduction in size of the ultrasonograph and a reduction in cost of the ultrasonograph.

CITATION LIST

Patent Literature

[Patent Literature 1] Japanese Publication of Unexamined Utility Model Application Jutsukaihei No. 6-38919 (1994) (Publication date: May 24, 1994)

SUMMARY OF INVENTION

Technical Problem

However, according to the probe connector disclosed in Patent Literature 1, the probe-side electrodes are each provided perpendicularly to an electrode retainer, and the housing-side electrodes are each similarly provided perpendicularly to an electrode retainer. Moreover, the drive motor causes the probe-side electrodes to move parallel to a surface of the electrode retainer on which surface the probe-side electrodes are provided. This causes a problem that those electrodes cannot be densely arranged, leading to an increase in size of an entire probe connector.

The present invention has been made in view of the above problems, and an object of the present invention is to downsize a connector by densely arranging first electrodes and second electrodes, while configuring the connector such that (i) a contact state, where the first electrodes are in contact with the respective second electrodes, and (ii) a non-contact state, where the first electrodes are not in contact with the respective second electrodes, can be switched inside the connector.

Solution to Problem

A connector device in accordance with an aspect of the present invention includes: a first connector including a plurality of first electrodes; a second connector including a plurality of second electrodes; and a drive part configured to cause a contact state and a non-contact state to be switched, by causing the plurality of first electrodes and/or the plurality of second electrodes to move parallel to a first direction in which the first connector and the second connector face each other, the contact state being a state where the plurality of first electrodes are in contact with the respective plurality of second electrodes, the non-contact state being a state where the plurality of first electrodes are not in contact with the respective plurality of second electrodes.

According to the above configuration, the contact state and the non-contact state are switched by causing the plurality of first electrodes and/or the plurality of second electrodes to move parallel to the first direction. This prevents (i) the plurality of first electrodes from coming into contact with each other and (ii) the plurality of second electrodes from coming into contact with each other, even in a case where the plurality of first electrodes and the plurality of second electrodes are densely arranged. This makes it possible to densely arrange electrodes and to downsize a connector device.

A connector device in accordance with an aspect of the present invention can be arranged such that each of the plurality of first electrodes includes a first urging member and/or each of the plurality of second electrodes includes a second urging member; and in the contact state, the each of the plurality of first electrodes is urged in the first direction by the first urging member and/or the each of the plurality of second electrodes is urged in the first direction by the second urging member.

According to the above configuration, even in a case where, for example, the plurality of first electrodes vary in height from a substrate when the plurality of first electrodes are mounted in the substrate, the first urging member is compressed in a case where the plurality of first electrodes are brought into contact with the respective plurality of second electrodes. This allows all of the plurality of first electrodes to be absolutely in contact with the respective plurality of second electrodes under substantially uniform pressure, and thereby makes it easier to mount the plurality of first electrodes in the substrate.

A connector device in accordance with an aspect of the present invention can be arranged such that each of the plurality of first electrodes has a needle shape; and the each of the plurality of first electrodes extends parallel to the first direction.

According to the above configuration, each of the plurality of first electrodes has a needle shape. This makes it possible to densely arrange the plurality of first electrodes and thereby downsize the connector device.

A connector device in accordance with an aspect of the present invention can be arranged such that the each of the plurality of first electrodes has a needle shape; the each of the plurality of first electrodes extends parallel to the first direction; and the each of the plurality of first electrodes includes: a contact part configured to be in contact with a corresponding one of the plurality of second electrodes; a base part located in a direction opposite to a direction in which the plurality of second electrodes are located, as viewed from the contact part; and a spring configured to serve as the first urging member, the spring being provided between the contact part and the base part.

According to the above configuration, the spring is provided between the contact part and the base part of each of the plurality of first electrodes each having a needle shape. Therefore, in a case where the contact part is brought into contact with a corresponding one of the plurality of second electrodes, the spring is compressed. This allows the plurality of first electrodes to be in contact with the respective plurality of second electrodes under substantially uniform pressure. It is therefore possible to absolutely bring the plurality of first electrodes into contact with the respective plurality of second electrodes.

A connector device in accordance with an aspect of the present invention can be arranged such that at least one of the first connector and the second connector includes a guide part configured to guide contact between the plurality of first electrodes and the respective plurality of second electrodes.

According to the above configuration, provision of the guide part prevents (i) the plurality of first electrodes from coming into contact with each other and/or with a foreign matter and (ii) the plurality of second electrodes from coming into contact with each other and/or with a foreign matter. Moreover, since the plurality of first electrodes are guided to be in contact with the respective plurality of second electrodes by the guide part, it is also possible to prevent each of the plurality of first electrodes from erroneously coming into contact with one of the plurality of second electrodes which one is different from the corresponding electrode.

A connector device in accordance with an aspect of the present invention can be arranged such that the drive part is configured to cause the plurality of first electrodes to move; the second connector includes recesses configured to serve as the guide part; and the plurality of second electrodes are provided on respective bottoms of the recesses.

According to the above configuration, it is possible for an operator to operate the connector device without touching the plurality of first electrodes and/or the plurality of second electrodes. This improves an operating life of the connector device.

Advantageous Effects of Invention

The present invention makes it possible to downsize a connector device configured to cause (i) a contact state, where first electrodes are in contact with respective second electrodes, and (ii) a non-contact state, where the first electrodes are not in contact with the respective second electrodes, to be switched inside the connector.

DESCRIPTION OF EMBODIMENTS

The following description will discuss, in detail, an embodiment of the present invention with reference to the drawings.

(Configuration of Switching Connector)

Figure 1:
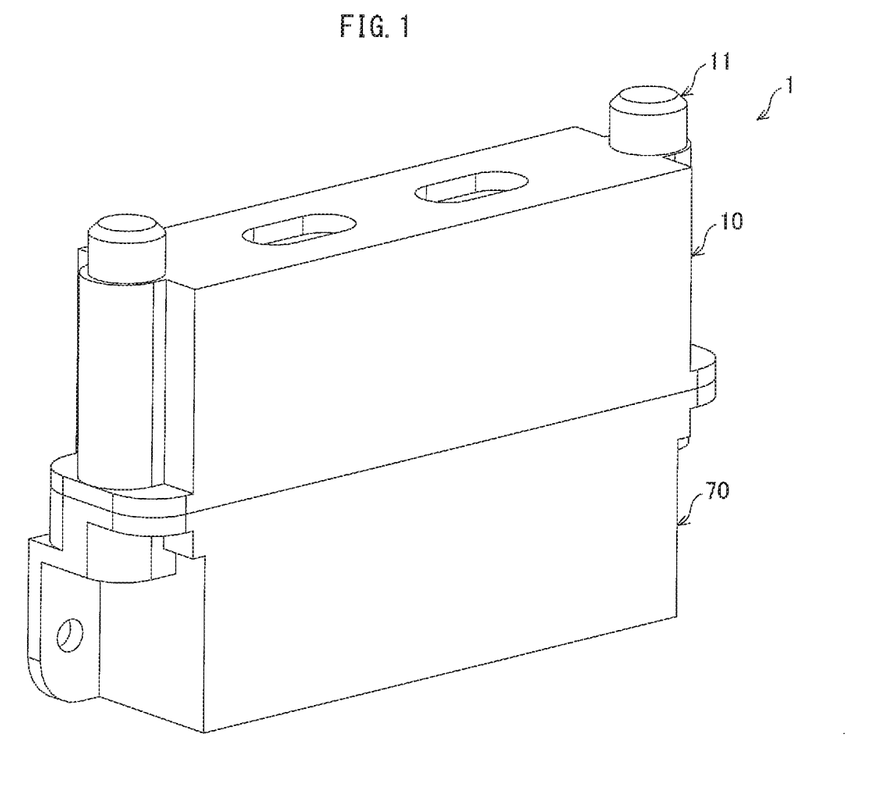
FIG. 1 is a perspective view of an appearance of a switching connector in accordance with an embodiment of the present invention.

FIG. 1 is a perspective view of an appearance of a switching connector (connector device) 1, via which a housing and an ultrasonic probe each included in an ultrasonograph are connected to each other, in accordance with an embodiment of the present invention. As illustrated in FIG. 1, the switching connector 1 includes a probe-side connector (first connector) 10, which is connected to the ultrasonic probe, and a housing-side connector (second connector) 70, which is connected to the housing. The probe-side connector 10 and the housing-side connector 70 are provided so as to face each other. Via the switching connector 1, the housing and the ultrasonic probe of the ultrasonograph can be electrically connected to each other. The probe-side connector 10 and the housing-side connector 70 are attachable to and detachable from each other by use of knurled screws 11 included in the probe-side connector 10.

For convenience, a direction in which the housing-side connector 70 is provided as viewed from the probe-side connector 10 will be hereinafter referred to as a downward direction, and a direction in which the probe-side connector 10 is provided as viewed from the housing-side connector 70 will be hereinafter referred to as an upward direction. A longitudinal direction of the switching connector 1 as viewed from above will be hereinafter referred to as a right-left direction.

Respective configurations of the probe-side connector 10 and the housing-side connector 70 will be described below.

(Configuration of Probe-Side Connector)

Figure 2:
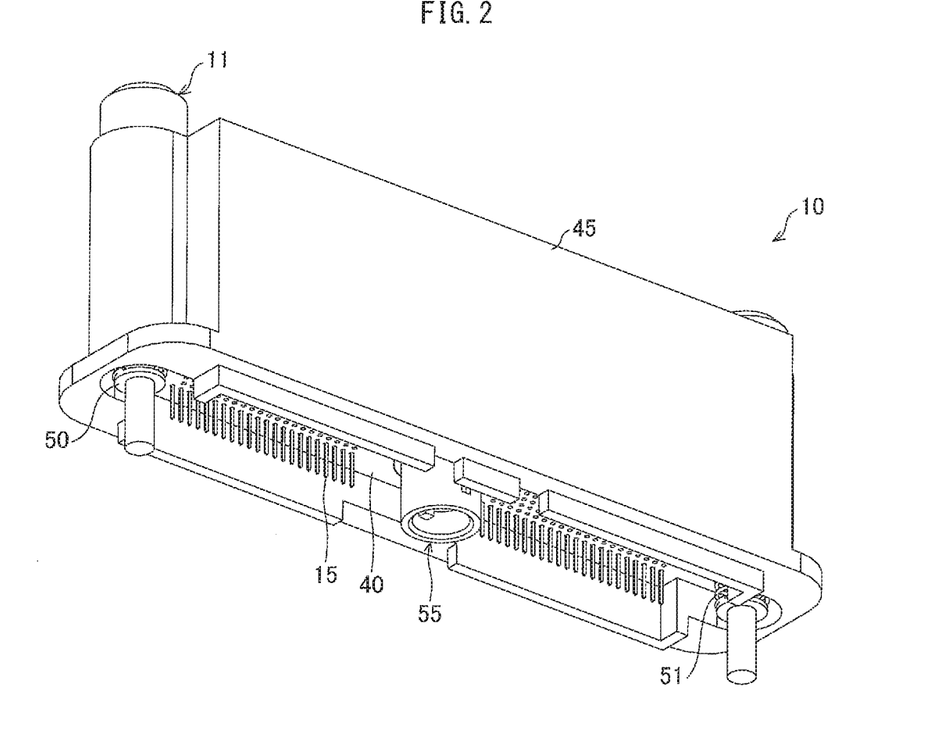
FIG. 2 is a perspective view of a probe-side connector of the switching connector illustrated in FIG. 1 as viewed from below.
Figure 3:
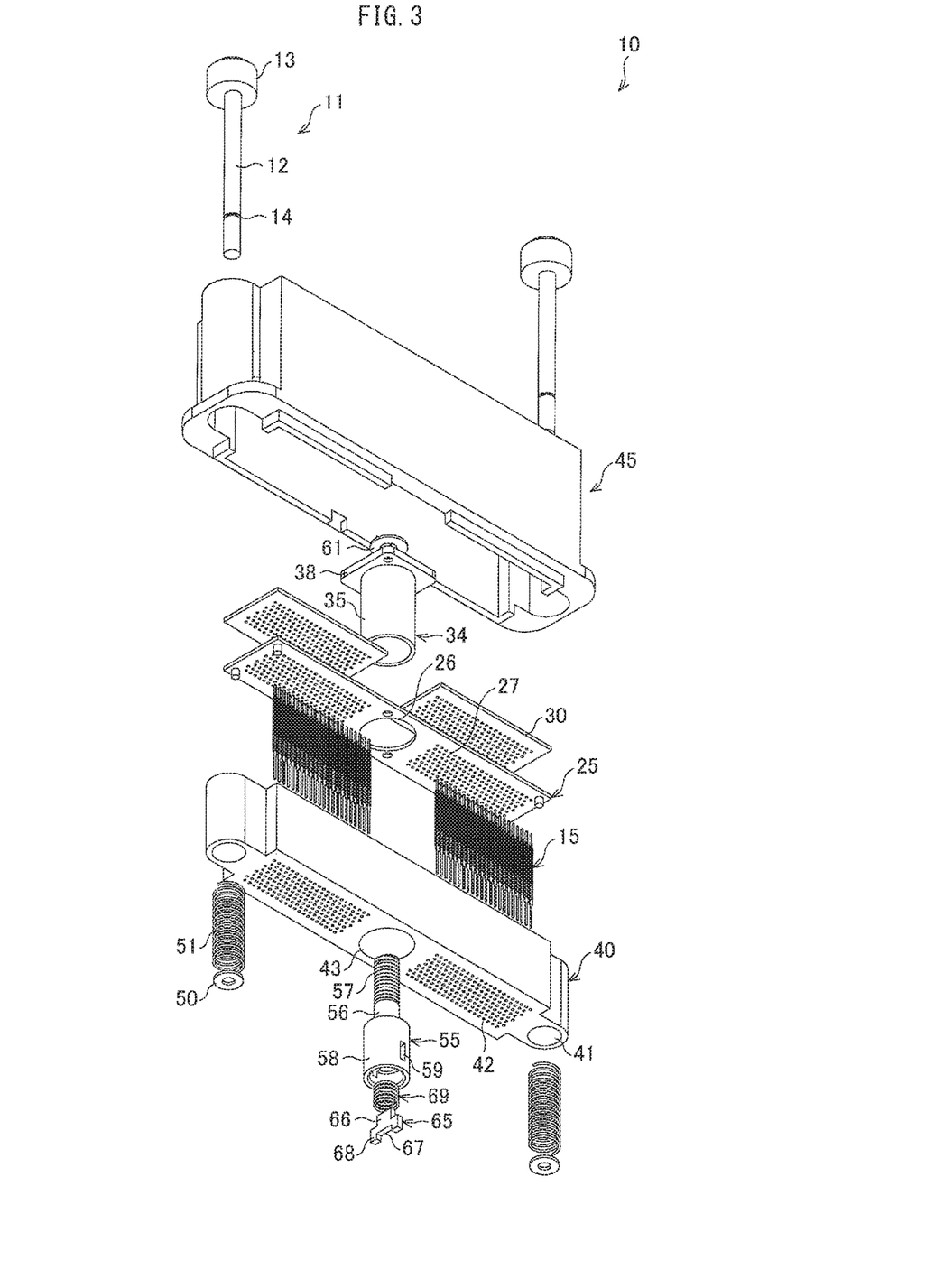
FIG. 3 is an exploded perspective view of the probe-side connector illustrated in FIG. 2.

FIG. 2 is a perspective view of the probe-side connector 10 as viewed from below. FIG. 3 is an exploded perspective view of the probe-side connector 10. As illustrated in FIGS. 2 and 3, the probe-side connector 10 includes the knurled screws 11, a probe-side casing 45, a drive shaft fixing ring 61, a drive housing 34, probe substrates 30, a probe fixing plate 25, a plurality of probe pins (first electrodes) 15 (only part of which is illustrated in FIGS. 2 and 3 and the subsequent drawings), a probe housing 40, return springs 51, spring washers 50, a drive shaft 55, a clutch spring 69, and a clutch plate 65.

Figure 4:
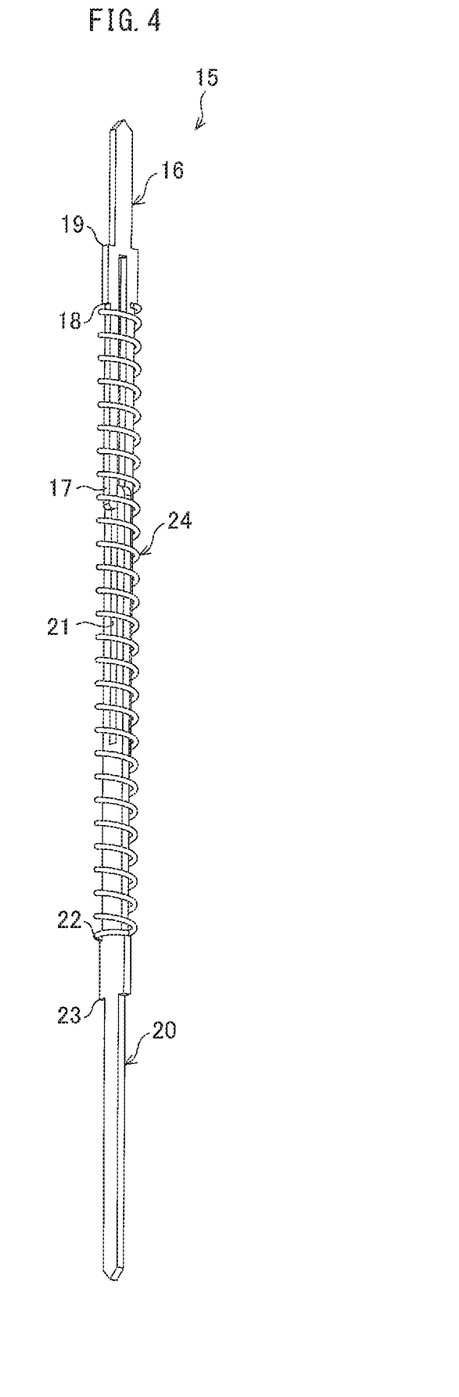
FIG. 4 is a perspective view of one of a plurality of probe pins illustrated in FIG. 3.

Each of the plurality of probe pins 15 is an electrode having a needle shape. The housing and the ultrasonic probe of the ultrasonograph are electrically connected to each other via the plurality of probe pins 15. FIG. 4 is a perspective view of one of the plurality of probe pins 15 illustrated in FIG. 3. As illustrated in FIG. 4, each of the plurality of probe pins 15 includes a first plate-shaped part (base part) 16, a second plate-shaped part (contact part) 20, and a probe spring (urging member) 24.

The first plate-shaped part 16 is two-forked so as to have two divided parts which extend downward and which have respective different lengths. A shorter one of the two divided parts has an engaging part 17 at a lower end thereof. The second plate-shaped part 20 has a long hole extending from a central portion thereof toward an upper end thereof. The first plate-shaped part 16 has probe spring supporting parts 18 each having a wall directed downward. The second plate-shaped part 20 has probe spring supporting parts 22 each having a wall directed upward. The first plate-shaped part 16 also has abutment parts 19 each having a wall directed upward and being located above the respective probe spring supporting parts 18. Similarly, the second plate-shaped part 20 also has abutment parts 23 each having a wall directed downward and being located below the respective probe spring supporting parts 22.

The first plate-shaped part 16 and the second plate-shaped part 20 are connected to each other at an angle of 90° so that the engaging part 17 of the first plate-shaped part 16 can engage with an upper end of an inner wall of the long hole 21 of the second plate-shaped part 20. A probe spring 24 is provided, between (i) the probe spring supporting parts 18 and (ii) the probe spring supporting parts 22 facing the respective probe spring supporting parts 18, in a state where the probe spring 24 is compressed. This causes the each of the plurality of probe pins 15 to be urged in a vertical direction, so that the engaging part 17 of the first plate-shaped part 16 engages with the long hole 21 of the second plate-shaped part 20. In a case where the each of the plurality of probe pins 15 is compressed against a returning force (urging force) of the probe spring 24, engagement of the engaging part 17 with the long hole 21 is released. As such, the each of the plurality of probe pins 15 is contractable in the vertical direction. Note here that the first plate-shaped part 16 is in contact with the second plate-shaped part 20 even in a case where the engagement is released. It is therefore possible to electrify each of the plurality of probe pins 15, even in a case where the each of the plurality of probe pins 15 is compressed.

The probe fixing plate 25 is a plate-shaped member, and a thickness direction of the probe fixing plate 25 corresponds to the vertical direction. The probe fixing plate 25 has, at a center thereof, a hole 26 extending in the thickness direction. The probe fixing plate 25 further has, on right and left sides of the hole 26, a plurality of probe holes 27 located so as to correspond to the respective plurality of probe pins 15. Each of the plurality of probe holes 27 has a diameter substantially equal to that of an upper end of the first plate-shaped part 16 of a corresponding one of the plurality of probe pins 15. The plurality of probe pins 15 are inserted in the respective plurality of probe holes 27 so that the abutment parts 19 of the first plate-shaped part 16 of each of the plurality of probe pins 15 abuts on a lower surface of the probe fixing plate 25.

The probe substrates 30 are a pair of plate-shaped members, and are provided on respective right and left sides so that they abut on an upper surface of the probe fixing plate 25 without blocking the hole 26 of the probe fixing plate 25. Each of the probe substrates 30 is electrically connected to corresponding ones of the plurality of probe pins 15 protruding from the respective plurality of probe holes 27 of the probe fixing plate 25.

The drive housing 34 includes a cylindrical part 35 and a flange part 38. The cylindrical part 35 is a cylindrical member, and has an outer diameter that matches an inner diameter of the hole 26 of the probe fixing plate 25. The cylindrical part 35 has a first cylindrical portion (not illustrated) and a second cylindrical portion (not illustrated) which is provided on the first cylindrical portion and which has an inner diameter smaller than that of the first cylindrical portion. The second cylindrical portion has an internal thread. The flange part 38, having a substantially square shape, is provided on an upper end of the cylindrical part 35.

The cylindrical part 35 of the drive housing 34 is inserted in the hole 26 of the probe fixing plate 25 so that the flange part 38 abuts on the probe fixing plate 25. The flange part 38 has screw holes. The flange part 38 is fixed to the probe fixing plate 25 by use of screws. This causes the probe fixing plate 25 and the drive housing 34 to be integrally driven.

The probe housing 40 is a substantially rectangular parallelepiped member, and is provided so as to guide movement of the plurality of probe pins 15. The probe housing 40 has return spring retaining holes 41, probe retaining holes 42, and a drive housing retaining hole 43.

The drive housing retaining hole 43 is a cylindrical hole, and is provided at a center of the probe housing 40 so as to extend in the vertical direction. The drive housing retaining hole 43 has an inner diameter substantially equal to the outer diameter of the cylindrical part 35 of the drive housing 34. The cylindrical part 35, which extends downward from the hole 26 of the probe fixing plate 25, is inserted in the drive housing retaining hole 43.

Each of the probe retaining holes 42 is a cylindrical hole, and is provided so as to extend in the vertical direction. The probe retaining holes 42 are located so as to correspond to the respective plurality of probe pins 15. Each of the probe retaining holes 42 has an inner diameter substantially equal to an outer diameter of a corresponding one of the plurality of probe pins 15. The plurality of probe pins 15 are provided in the respective probe retaining holes 42 so that the abutment parts 23 of each of the plurality of probe pins 15 abut on an inner bottom surface of the probe housing 40. This causes the movement of the plurality of probe pins 15 to be guided.

The return spring retaining holes 41 are a pair of holes, and are provided on respective right and left sides so as to be located on respective outer sides of a region in which the probe retaining holes 42 are provided. Each of the return spring retaining holes 41 also has a cylindrical shape, and extends in the vertical direction. Each of the return spring retaining holes 41 has, at an upper end thereof, a wall (not illustrated) which projects inward so that an inner diameter of the each of the return spring retaining holes 41 is smaller at the upper end.

The probe-side casing 45 has a substantially rectangular parallelepiped shape, and has a bottom which is open. The probe-side casing 45 has an inner shape that matches a shape of the probe housing 40. The probe housing 40 is provided inside the probe-side casing 45. The probe fixing plate 25, the probe substrates 30, and the drive housing 34 are retained between the probe housing 40 and the probe-side casing 45. The probe-side casing 45 has, in an upper end surface thereof, holes located so as to correspond to the respective return spring retaining holes 41 of the probe housing 40. Each of the holes has a diameter smaller than that of a corresponding one of the return spring retaining holes 41.

Each of the knurled screws 11 has (i) a columnar part 12 having a rod shape and (ii) a screw head 13 provided on an upper end of the columnar part 12. As described earlier, the knurled screws 11 are used to fix the probe-side connector 10 to the housing-side connector 70. As such, each of the knurled screws 11 is provided so that (i) a lower end of the screw head 13 abuts on the upper end surface of the probe-side casing 45 and (ii) the columnar part 12 protrudes from the bottom of the probe-side casing 45 through a corresponding one of the holes of the probe-side casing 45 and through a corresponding one of the return spring retaining holes 41 of the probe housing 40. The columnar part 12 has, at a position slightly above a lower end thereof, a circular groove 14 in which a corresponding one of the spring washers 50, each having a ring shape, is provided. Each of the knurled screws 11 has an external thread at a portion below the circular groove 14.

Each of the return springs 51 is a coil spring, and is provided around the columnar part 12 of a corresponding one of the knurled screws 11 in a state where the each of the return springs 51 is compressed so as to be shorter than a natural length thereof. A lower end of each of the return springs 51 is supported by a corresponding one of the spring washers 50, and an upper end of each of the return springs 51 is supported by the wall of a corresponding one of the return spring retaining holes 41 of the probe housing 40, which wall projects inward.

The drive shaft 55 has a first shaft part 56 and a second shaft part 58. The first shaft part 56 has a columnar shape, and has an outer diameter equal to the inner diameter of the second cylindrical portion of the drive housing 34. The first shaft part 56 has, on an outer periphery thereof, an external thread that matches the internal thread of the second cylindrical portion. The drive shaft 55 is screwed in the drive housing 34. The first shaft part 56 has a circular groove 57 in a vicinity of an upper end thereof. The drive shaft 55 is provided so that a region of the first shaft part 56 in which region the circular groove 57 is provided protrudes from the flange part 38 of the drive housing 34. The drive shaft fixing ring 61 is provided in the circular groove 57.

The second shaft part 58 is a cylindrical member, and is provided under the first shaft part 56 so as to be coaxially adjacent to the first shaft part 56. The second shaft part 58 has an outer diameter greater than that of the first shaft part 56. The first shaft part 56 and the second shaft part 58 thus have a difference in thickness therebetween. The second shaft part 58 has an outer diameter that matches the inner diameter of the first cylindrical portion of the drive housing 34. The second shaft part 58 has, in a periphery thereof, two vertical grooves 59 which are provided symmetrically with respect to an axis. The second shaft part 58 has an inner diameter which is smaller at a portion extending upward from respective upper ends of the vertical grooves 59. Such a portion constitutes a small diameter part 64 (see FIG. 7).

The clutch plate 65 is a plate member, and has an upper part 66, a lower part 67, and downwardly-suspended parts 68. The upper part 66 and the lower part 67 together make a raised shape (T-shape). The two downwardly-suspended parts 68 extend downward from respective ends, in a width direction, of the lower part 67. The clutch plate 65 is provided inside the second shaft part 58 of the drive shaft 55. The lower part 67 of the clutch plate 65 has a width slightly greater than the inner diameter of the second shaft part 58. Therefore, the lower part 67 is partially fitted in the vertical grooves 59 of the second shaft part 58, and the downwardly-suspended parts 68 are also partially fitted in the respective vertical grooves 59 of the second shaft part 58.

The clutch spring 69 is a coil spring, and is provided between an outer surface of the upper part 66 of the clutch plate 65 and an inner surface of the second shaft part 58 in a state where clutch spring 69 is compressed. An upper end of the clutch spring 69 is supported by the small diameter part 64 of the second shaft part, and a lower end of the clutch spring 69 is supported by the lower part 67 of the clutch plate 65. This causes lower ends of the downwardly-suspended parts 68 to partially abut on respective lower ends of the vertical grooves 59, so that the clutch plate 65 is retained.

(Configuration of Housing-Side Connector)

Figure 5:
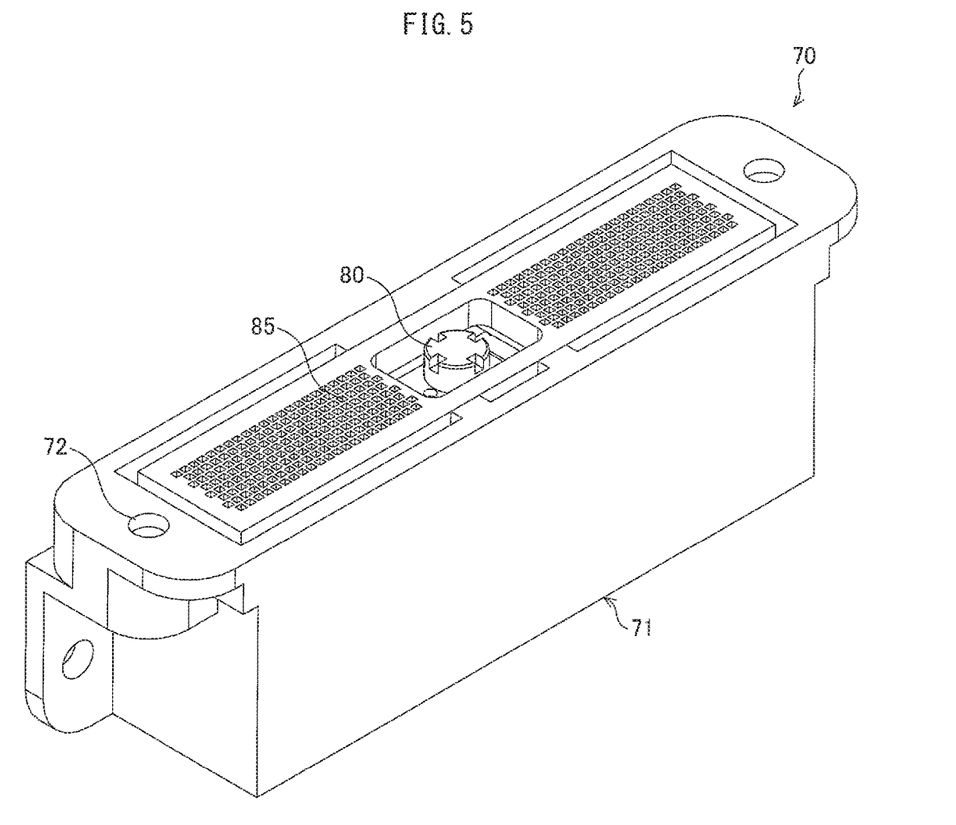
FIG. 5 is a perspective view of a housing-side connector of the switching connector illustrated in FIG. 1 as viewed from above.
Figure 6:
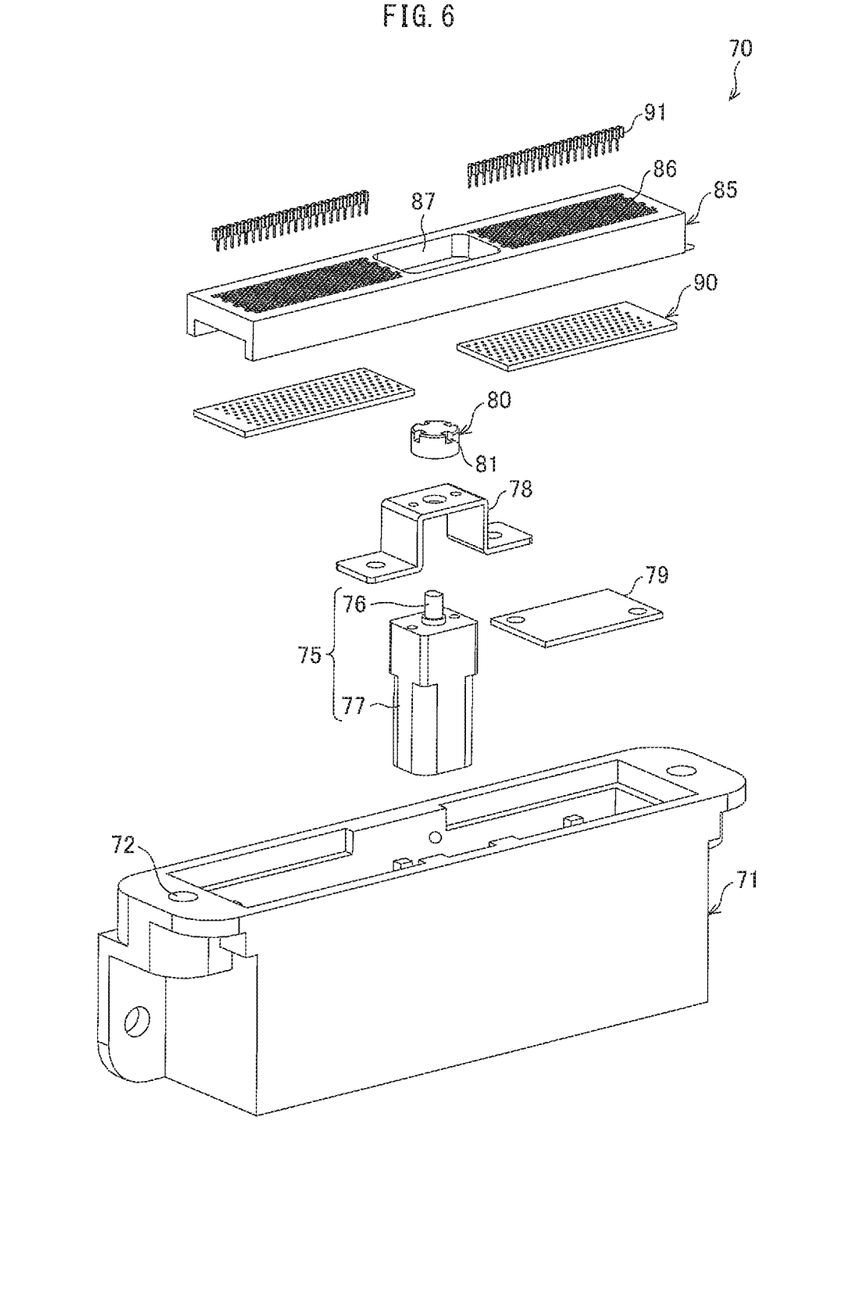
FIG. 6 is an exploded perspective view of the housing-side connector illustrated in FIG. 5.

FIG. 5 is a perspective view of the housing-side connector 70 as viewed from above. FIG. 6 is an exploded perspective view of the housing-side connector 70. As illustrated in FIGS. 5 and 6, the housing-side connector 70 includes a housing-side casing 71, a motor (drive part) 75, a motor bracket 78, a connection clutch 80, electrode substrates 90, an electrode housing (guide part) 85, and a plurality of electrode pads (second electrodes) 91 (only part of which is illustrated in FIGS. 5 and 6 and the subsequent drawings).

The housing-side casing 71 is a hollow casing having a substantially rectangular parallelepiped shape, and has an upper end which is open. The motor 75, the motor bracket 78, the connection clutch 80, the electrode substrates 90, the electrode housing 85, and the plurality of electrode pads 91 are provided inside and supported by the housing-side casing 71. An upper surface of the housing-side casing 71 has a shape which matches that of a lower surface of the probe-side casing 45. The housing-side casing 71 has, in the upper surface thereof, screw holes 72 located so as to correspond to the respective knurled screws 11. Each of the screw holes 72 has a diameter substantially equal to an outer diameter of the columnar part 12 of a corresponding one of the knurled screws 11. The knurled screws 11 are screwed in the respective screw holes 72 so that the probe-side connector 10 is fixed to the housing-side connector 70.

The motor 75 causes a contact state, where the plurality of probe pins 15 are in contact with the respective plurality of electrode pads 91, and a non-contact state, where the plurality of probe pins 15 are not in contact with the respective plurality of electrode pads 91, to be switched. The motor 75 has a rotation shaft 76, having a substantially columnar shape, and a base part 77. The motor 75 is fixed by the motor bracket 78. Specifically, the motor bracket 78 is screwed to the housing-side casing 71 so as to cover the base part 77 of the motor 75. A control substrate 79 controls operation of the motor 75. Specifically, the motor 75 is configured such that the rotation shaft 76 rotates in accordance with a signal supplied from the control substrate 79.

The connection clutch 80 is a substantially columnar member, and is attached to the rotation shaft of the motor 75. By operation of the motor 75, the connection clutch 80 is caused to rotate integrally with the rotation shaft 76. The connection clutch 80 has an outer diameter substantially equal to the inner diameter of the second shaft part 58 of the drive shaft 55. The connection clutch 80 has, at an upper end thereof, four notches 81 provided at 90° intervals along an outer periphery thereof. The notches 81 are shaped so that any opposed ones of the notches 81 match the respective downwardly-suspended parts 68 of the clutch plate 65.

The electrode housing 85 has a substantially rectangular-parallelepiped shape, and has a plurality of electrode holes (recesses) 86 located so as to correspond to the respective plurality of probe pins 15. The electrode housing 85 also has a hollow 87 located so as to correspond to the connection clutch 80 and the motor 75. Specifically, the rotation shaft 76 of the motor 75 and the connection clutch 80 are provided in the hollow 87.

The electrode substrates 90 are a pair of substrates, and are provided on respective right and left sides, as with the probe substrates 30, so that respective upper surfaces of the electrode substrates 90 are in contact with a lower surface of the electrode housing 85 without blocking the hollow 87 of the electrode housing 85.

The plurality of electrode pads 91 are provided on respective inner bottoms of the plurality of electrode holes 86 of the electrode housing 85. Each of the electrode substrates 90 is connected to corresponding ones of the plurality of electrode pads 91. Contact between the plurality of electrode pads 91 and the respective plurality of probe pins 15 causes electrical connection between the probe-side connector 10 and the housing-side connector 70 of the switching connector 1.

(How Probe-Side Connector is Connected to Housing-Side Connector)

How the probe-side connector 10 is connected to the housing-side connector 70 and how the plurality of electrode pads 91 are brought into contact with the respective plurality of probe pins 15 will be described below.

The probe-side connector 10 and the housing-side connector 70 are connected to each other by (i) use of the knurled screws 11 and (ii) fitting of the connection clutch 80 with the clutch plate 65.

The knurled screws 11 are screwed into the respective screw holes 72 of the housing-side casing 71 so that the probe-side casing 45 is fixed to the housing-side casing 71. This causes the probe-side connector 10 and the housing-side connector 70 to be connected to each other.

Next, how the probe-side connector 10 and the housing-side connector 70 are connected to each other by fitting of the connection clutch 80 with the clutch plate 65 will be described below.

Figure 7:
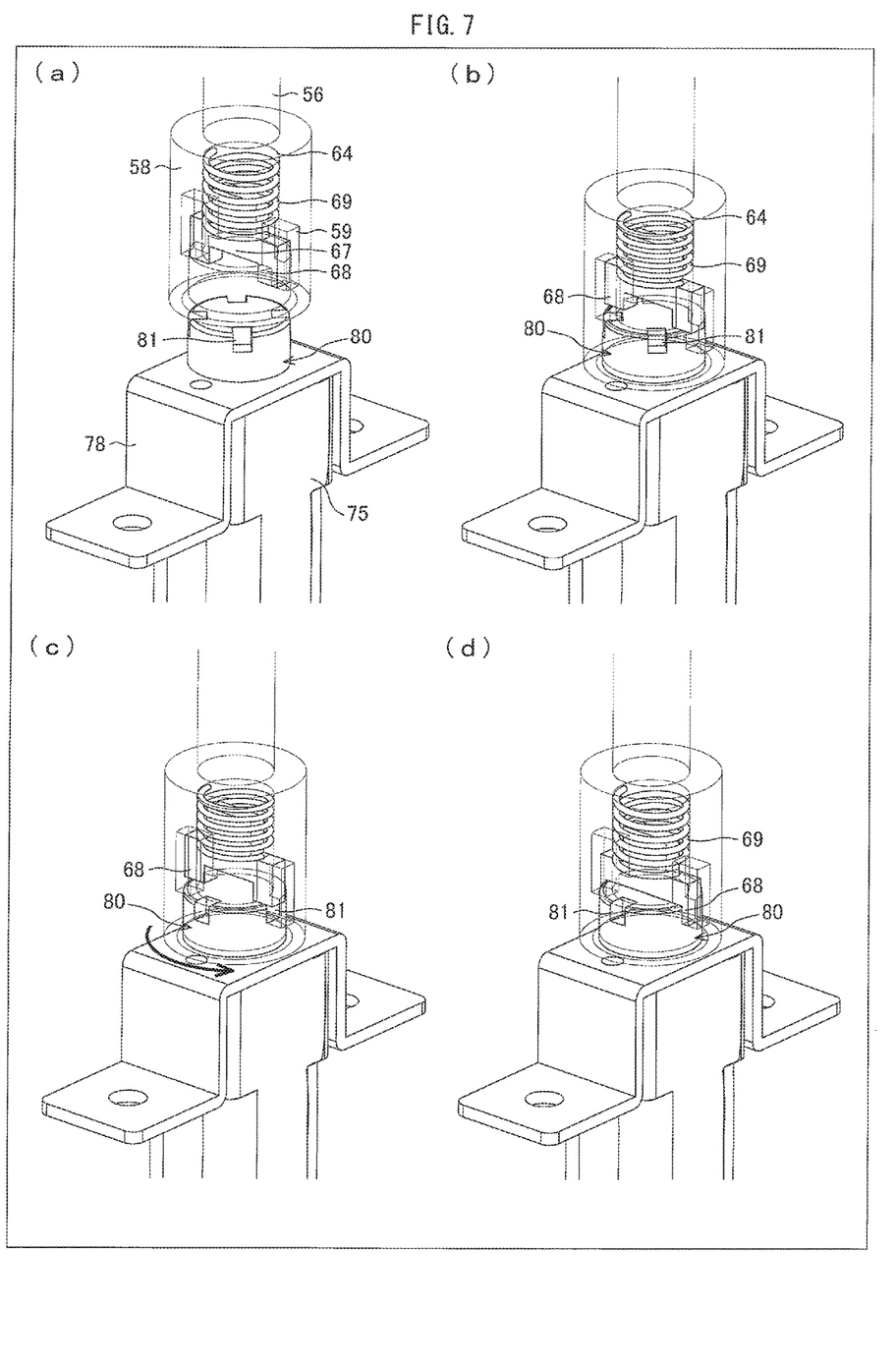
FIG. 7 is a view illustrating how a motor of the housing-side connector illustrated in FIG. 5 causes a connection clutch to be fitted with a clutch plate. (a) of FIG. 7 illustrates a state where the probe-side connector and the housing-side connector have not been connected to each other yet by use of knurled screws. (b) of FIG. 7 illustrates a state where the probe-side connector and the housing-side connector have been connected to each other by use of the knurled screws. (c) of FIG. 7 illustrates a state where the motor has started to operate. (d) of FIG. 7 illustrates a state where fitting of the clutch plate and the connection clutch has been completed.

FIG. 7 is a view illustrating how the motor 75 causes the connection clutch 80 to be fitted with the clutch plate 65. (a) of FIG. 7 illustrates a state where the probe-side connector 10 and the housing-side connector 70 have not been connected to each other yet by use of the knurled screws 11. (b) of FIG. 7 illustrates a state where the probe-side connector 10 and the housing-side connector 70 have been connected to each other by use of the knurled screws 11. (c) of FIG. 7 illustrates a state where the motor 75 has started to operate. (d) of FIG. 7 illustrates a state where fitting of the connection clutch 80 with the clutch plate 65 has been completed.

As illustrated in (a) of FIG. 7, in the state where the probe-side connector 10 and the housing-side connector 70 have not been connected to each other yet by use of the knurled screws 11, the clutch plate 65 is urged downward by the clutch spring 69. This causes the downwardly-suspended parts 68 of the clutch plate 65 to be in contact with the respective vertical grooves 59 of the second shaft part 58 of the drive shaft 55.

As illustrated in (b) of FIG. 7, in a case where connection between the probe-side connector 10 and the housing-side connector 70 has been completed by use of the knurled screws 11, the connection clutch 80 is arranged inside the second shaft part 58. This causes the connection clutch 80 to push the clutch plate 65 upward, so that the clutch spring 69 is compressed more tightly.

As illustrated in (c) of FIG. 7, the rotation shaft 76 of the motor 75 starts to rotate once the motor 75 starts to operate. This causes the connection clutch 80 to rotate, integrally with the rotation shaft 76, in a direction indicated by an arrow in (c) of FIG. 7. Then, when the rotation shaft 76 of the motor 75 has rotated by a certain angle, any opposed ones of the notches 81 of the connection clutch 80 are fitted with the respective downwardly-suspended parts 68 of the clutch plate 65 (see (d) of FIG. 7). This causes operation (rotation) of the motor 75 to be transmitted to the drive shaft 55 via the connection clutch 80 and the clutch plate 65. For convenience, rotation of the rotation shaft 76 of the motor 75 in the direction indicated by the arrow in (c) of FIG. 7 will be hereinafter referred to as normal rotation (or rotation in a normal direction), and rotation of the rotation shaft 76 in an opposite direction will be hereinafter referred to as a reverse rotation (or rotation in a reverse direction).

In a case where the rotation shaft 76 of the motor 75 further rotates in the normal direction while the any opposed ones of the notches 81 of the connection clutch 80 are fitted with the respective downwardly-suspended parts 68 of the clutch plate 65, the connection clutch 80, the clutch plate 65, and the drive shaft 55 are caused to rotate integrally with the rotation shaft 76. Since the first shaft part 56 of the drive shaft 55 is screwed in the second cylindrical part of the drive housing 34, such normal rotation of the drive shaft 55 causes the drive housing 34 to move downward. Accordingly, the probe substrates 30, the probe fixing plate 25, the plurality of probe pins 15, and the probe housing 40, all of which are arranged so as to move integrally with the drive housing 34, are also caused to move downward. The return spring 51 is compressed in accordance with movement of the probe housing 40.

Figure 8:
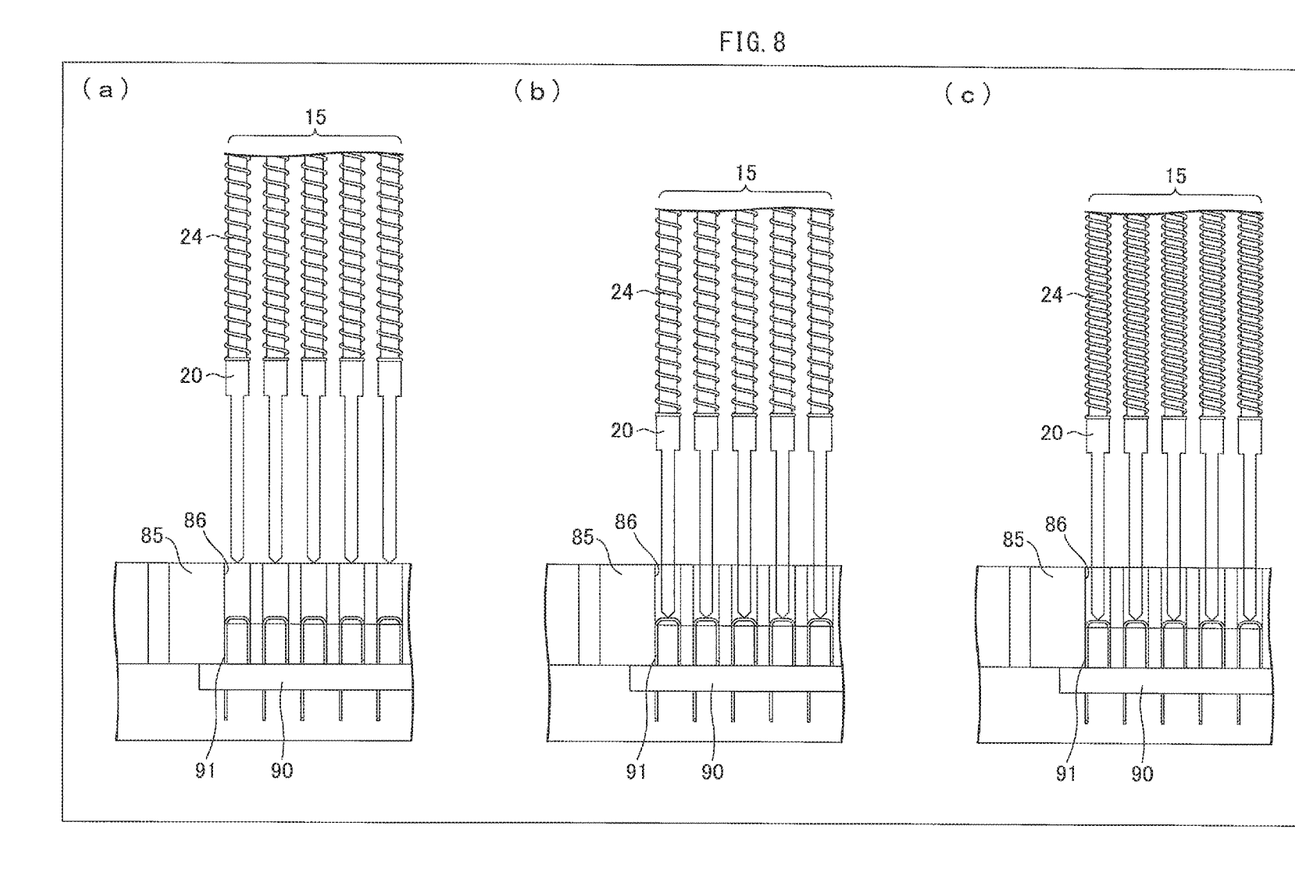
FIG. 8 is a view illustrating how probe pins are brought into contact with respective electrode pads. (a) of FIG. 8 illustrates a state where the probe pins have not been brought into contact with the respective electrode pads. (b) of FIG. 8 illustrates a state where the probe pins have been brought into contact with the respective electrode pads. (c) of FIG. 8 illustrates a state where the motor has further rotated in a normal direction while the probe pins are in contact with the respective electrode pads.

FIG. 8 is a view illustrating how the plurality of probe pins 15 are brought into contact with the respective plurality of electrode pads 91. (a) of FIG. 8 illustrates a state where the plurality of probe pins 15 have not been brought into contact with the respective plurality of electrode pads 91 yet, (b) of FIG. 8 illustrates a state where the plurality of probe pins 15 have been brought into contact with the respective plurality of electrode pads 91, and (c) of FIG. 8 illustrates a state where the rotation shaft 76 has further rotated in the normal direction while the plurality of probe pins 15 are in contact with the respective plurality of electrode pads 91.

(a) of FIG. 8 illustrates a positional relationship between the plurality of probe pins 15 and the plurality of electrode pads 91 in the state where the plurality of probe pins 15 have not been brought into contact with the respective plurality of electrode pads 91 yet. When any opposed ones of the notches 81 of the connection clutch 80 have been fitted with the respective downwardly-suspended parts 68 of the clutch plate 65, the plurality of probe pins 15 are still away from the respective plurality of electrode pads 91 by a given distance (see (a) of FIG. 8).

In a case where the rotation shaft 76 further rotates in the normal direction while the any opposed ones of the notches 81 of the connection clutch 80 are fitted with the respective downwardly-suspended parts 68 of the clutch plate 65, the plurality of probe pins 15 are caused to enter the respective plurality of electrode holes 86 of the electrode housing 85, and are guided to the respective plurality of electrode holes 86. This causes the plurality of probe pins 15 to be in contact with the respective plurality of electrode pads 91 (see (b) of FIG. 8).

In a case where, in the state illustrated in (b) of FIG. 8, the rotation shaft 76 further rotates in the normal direction, the probe fixing plate 25 and the probe housing 40 are caused to further move downward, and the first plate-shaped part 16 of each of the plurality of probe pins 15 is accordingly pressed downward (see (c) of FIG. 8). This causes the probe spring 24 to be compressed. It follows that an urging force of the probe spring 24 then causes the second plate-shaped part 20 of each of the plurality of probe pins 15 to be in contact with a corresponding one of the plurality of electrode pads 91 under a given pressure.

In a case where the rotation shaft 76 of the motor 75 is caused, in the state illustrated in (c) of FIG. 8, to rotate in the reverse direction, an operation opposite to that discussed above is conducted. That is, in a case where the rotation shaft 76 rotates in the reverse direction, the probe fixing plate 25 and the probe housing 40 are caused to move upward, and contact between the plurality of probe pins 15 and the respective plurality of electrode pads 91 is accordingly released. As such, the switching connector 1 of the present embodiment is configured such that the contact state and the non-contact state can be switched inside the switching connector 1 by causing the rotation shaft 76 of the motor 75 to rotate in the normal direction or the reverse direction.

Figure 9:
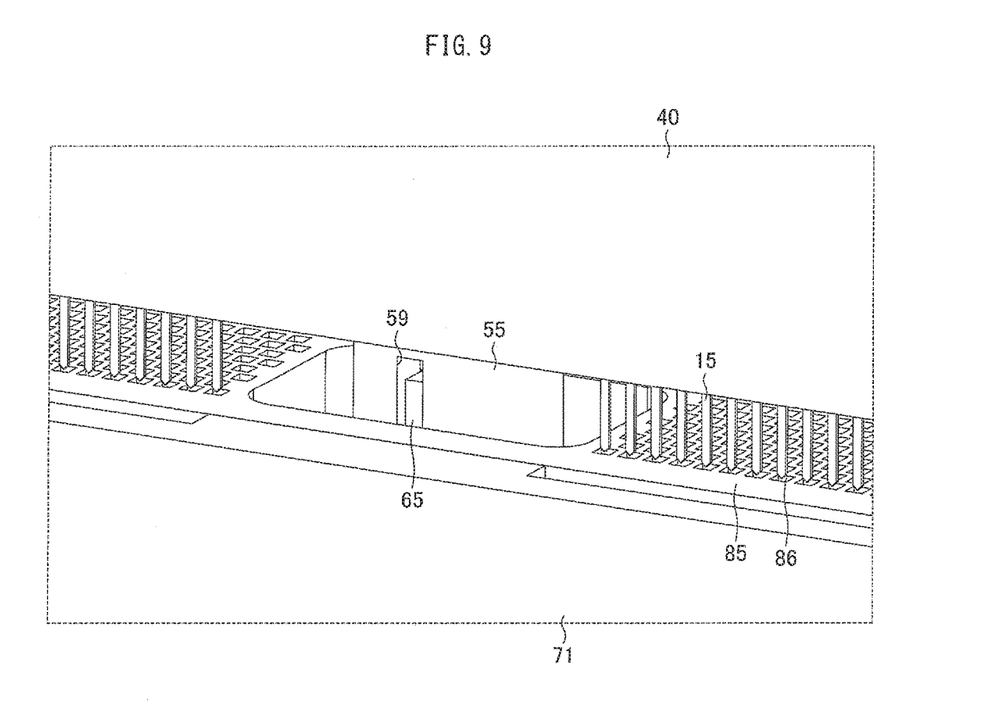
FIG. 9 is a partial perspective view illustrating a positional relationship between the probe pins and an electrode housing illustrated in (a) of FIG. 8.

FIG. 9 is a partial perspective view illustrating a positional relationship between the plurality of probe pins 15 and the electrode housing 85 illustrated in (a) of FIG. 8.

Note that it is difficult to mount the plurality of probe pins 15 in the probe substrates 30 so that the plurality of probe pins 15 do not vary in height (positions of tips of second plate-shaped parts 20) and inclination. To address this problem, the electrode housing 85 has the plurality of electrode holes 86 located so as to correspond to the respective plurality of probe pins 15 (see FIGS. 8 and 9). Therefore, in a case where the motor 75 starts to operate, the plurality of probe pins 15 are guided to the respective plurality of electrode holes 86 so as to come into contact with the respective plurality of electrode pads 91. As such, since the plurality of probe pins 15 are guided to the respective plurality of electrode holes 86, it is possible to cause the plurality of probe pins 15 to be absolutely in contact with the respective plurality of electrode pads 91 even in a case where the plurality of probe pins 15 vary in inclination to some extent. Furthermore, in a case where the plurality of probe pins 15 which have been brought into contact with the respective plurality of electrode pads 91 are further pressed so that the probe spring 24 of each of the plurality of probe pins 15 is compressed, a length of the each of the plurality of probe pins 15 becomes shorter. This allows the plurality of probe pins 15 to be absolutely in contact with the respective plurality of electrode pads 91, even in a case where the plurality of probe pins 15 vary in height and/or inclination to some extent when the plurality of probe pins 15 are mounted in the probe substrates 30. This makes it easier to mount the plurality of probe pins 15 in the probe substrates 30.

Provision of the plurality of electrode holes 86 causes the plurality of electrode pads 91 not to be exposed from the upper surface of the housing-side casing 71. This allows an operator to operate the switching connector 1 without touching the plurality of electrode pads 91. Provision of the plurality of electrode holes 86 also allows the plurality of electrode pads 91 to be prevented from coming into contact with a foreign matter. This makes it possible to prevent deterioration of the plurality of electrode pads 91 and thereby improve an operating life of the switching connector 1.

Since the plurality of electrode holes 86 are provided in which the respective plurality of electrode pads 91 are provided, it is possible to prevent contact between the plurality of electrode pads 91 and contact between the plurality of probe pins 15. This makes it possible to more densely arrange the plurality of electrode pads 91 and the plurality of probe pins 15 so as to downsize the switching connector 1.

According to the above embodiment, the switching connector 1 is configured such that (i) the motor 75 is included in the housing-side connector 70 and (ii) in a case where the motor 75 starts to operate, the plurality of probe pins 15 are caused, via the drive shaft, to move. However, the switching connector 1 is not limited to such a configuration, and can be alternatively configured such that (i) the motor 75 is included in the probe-side connector 10 and (ii) the plurality of electrode pads 91 are caused to move. The switching connector 1 can also be alternatively configured such that the plurality of probe pins 15 and the plurality of electrode pads 91 are both caused to move.

Furthermore, the switching connector 1 can also be alternatively configured such that (i) the housing-side connector 70 includes the plurality of probe pins 15 and (ii) the probe-side connector 10 includes the plurality of electrode holes 86 and the plurality of electrode pads 91.

The present invention is not limited to the descriptions of the above embodiment, and may be altered by a skilled person within the scope of the claims. An embodiment based on a proper combination of technical means disclosed in different embodiments is encompassed in the technical scope of the present invention.

INDUSTRIAL APPLICABILITY

The present invention is applicable to a connector device via which a probe and a main device of an ultrasonograph are connected.

REFERENCE SIGNS LIST

1 Switching connector (connector device)
10 Probe-side connector (first connector)
15 Probe pin (first electrode)
16 First plate-shaped part (base part)
20 Second plate-shaped part (contact part)
24 Probe spring (urging member)
40 Probe housing
70 Housing-side connector (second connector)
75 Motor (drive part)

85 Electrode housing (guide part)
86 Electrode holes (Recesses)
91 Electrode pad (second electrode)

The invention claimed is:

1. A connector device, comprising:
   a first connector including a plurality of first electrodes;
   a second connector including a plurality of second electrodes; and
   a screw for fixing the first connector and the second connector to each other in a connection state in which the first connector and the second connector are connected with each other;
   a drive part configured to cause a contact state and a non-contact state to be switched in the connection state of the first connector and the second connector, by causing the plurality of first electrodes and/or the plurality of second electrodes to move parallel to a first direction in which the first connector and the second connector face each other,
   the contact state being a state where the plurality of first electrodes are in contact with the respective plurality of second electrodes,
   the non-contact state being a state where the plurality of first electrodes are not in contact with the respective plurality of second electrodes,
   each of the plurality of first electrodes including a first urging member and/or each of the plurality of second electrodes including a second urging member; and
   in the contact state, the each of the plurality of first electrodes being urged in the first direction by the first urging member and/or the each of the plurality of second electrodes being urged in the first direction by the second urging member.

2. The connector device as set forth in claim 1, wherein:
   the each of the plurality of first electrodes has a needle shape; and
   the each of the plurality of first electrodes extends parallel to the first direction.

3. The connector device as set forth in claim 1, wherein:
   the each of the plurality of first electrodes has a needle shape;
   the each of the plurality of first electrodes extends parallel to the first direction; and
   the each of the plurality of first electrodes includes:
      a contact part configured to be in contact with a corresponding one of the plurality of second electrodes;
      a base part located in a direction opposite to a direction in which the plurality of second electrodes are located, as viewed from the contact part; and
      a spring configured to serve as the first urging member, the spring being provided between the contact part and the base part.

4. The connector device as set forth in claim 1, wherein:
   at least one of the first connector and the second connector includes a guide part configured to guide contact between the plurality of first electrodes and the respective plurality of second electrodes.

5. The connector device as set forth in claim 4, wherein:
   the drive part is configured to cause the plurality of first electrodes to move;
   the second connector includes recesses configured to serve as the guide part; and
   the plurality of second electrodes are provided on respective bottoms of the recesses.

6. The connector device as set forth in claim 2, wherein:
   at least one of the first connector and the second connector includes a guide part configured to guide contact between the plurality of first electrodes and the respective plurality of second electrodes.

7. The connector device as set forth in claim 3, wherein:
   at least one of the first connector and the second connector includes a guide part configured to guide contact between the plurality of first electrodes and the respective plurality of second electrodes.

8. The connector device as set forth in claim 6, wherein:
   the drive part is configured to cause the plurality of first electrodes to move;
   the second connector includes recesses configured to serve as the guide part; and
   the plurality of second electrodes are provided on respective bottoms of the recesses.

9. The connector device as set forth in claim 7, wherein:
   the drive part is configured to cause the plurality of first electrodes to move;
   the second connector includes recesses configured to serve as the guide part; and
   the plurality of second electrodes are provided on respective bottoms of the recesses.

10. The connector device as set forth in claim 1, wherein the drive part is a motor.

11. The connector device as set forth in claim 10, wherein:
    the first connector includes a first clutch member;
    the second connector includes a second clutch member;
    in the connection state, the first clutch member is urged toward the second clutch member; and
    in the connection state, the second clutch member transmits rotation of the motor to the first clutch member.

12. The connector device as set forth in claim 11, wherein:
    in the connection state, the first clutch member is fitted with the second clutch member.

* * * * *